United States Patent [19]

McAllester

[11] Patent Number: 4,598,458

[45] Date of Patent: Jul. 8, 1986

[54] SURGICAL DRAPE WITH FLUID COLLECTION BAG

[75] Inventor: Spears L. McAllester, Fairfield, Ohio

[73] Assignee: The Kendall Company, Boston, Mass.

[21] Appl. No.: 488,918

[22] Filed: Apr. 27, 1983

[51] Int. Cl.$^4$ ............................................... A61F 13/00
[52] U.S. Cl. ............................................ 128/132 D; 604/357
[58] Field of Search ............. 604/357, 356, 355, 327, 604/317; 128/132 R, 132 D

[56] References Cited

U.S. PATENT DOCUMENTS

| | | |
|---|---|---|
| 759,084 | 5/1904 | Eggers et al. |
| 1,741,837 | 12/1929 | Gilbert. |
| 1,741,838 | 12/1929 | Gilbert. |
| 3,199,507 | 8/1965 | Kamm .................... 128/2 |
| 3,364,928 | 1/1968 | Creager, Jr. et al. ............ 128/132 |
| 3,386,444 | 6/1968 | Brenner et al. ............. 128/292 |
| 3,397,692 | 8/1968 | Creager, Jr. et al. ........... 128/132 D |
| 3,416,520 | 12/1968 | Creager, Jr. .............. 128/132 D |
| 3,575,225 | 4/1971 | Muheim ..................... 150/8 |
| 3,650,267 | 3/1972 | Anderson ................ 128/132 |
| 3,763,857 | 10/1973 | Schrading ............... 128/132 D |
| 3,791,382 | 2/1974 | Collins ................. 128/132 D |
| 3,911,912 | 10/1975 | Krebs et al. ............ 128/132 D |
| 3,920,179 | 11/1975 | Hall ...................... 604/317 |
| 3,952,738 | 4/1976 | Krzewinski ............ 128/132 D |
| 3,955,569 | 5/1976 | Krzewinski et al. ........... 128/132 D |
| 4,007,741 | 2/1977 | Waldrop et al. .............. 128/292 |
| 4,036,235 | 7/1977 | Hathaway .................. 128/292 |
| 4,169,472 | 10/1979 | Morris .................... 128/132 D |
| 4,201,212 | 5/1980 | Bradley ................... 128/275 |
| 4,221,371 | 9/1980 | Kuphal .................... 604/356 |
| 4,323,062 | 4/1982 | Canty .................... 128/132 D |
| 4,336,797 | 6/1982 | Latucca et al. ............. 128/132 D |

OTHER PUBLICATIONS

Brochure: "Steri-Drape Irrigation Pouch" from Surgical Products Division/3M Company.

*Primary Examiner*—C. Fred Rosenbaum
*Assistant Examiner*—Gene B. Kartchner
*Attorney, Agent, or Firm*—Donald N. Halgren

[57] ABSTRACT

A surgical drape has an upper surface and a surgical site, and has a fluid collection bag attached to the upper surface. The bag has a first opening, a lower, fluid-collection chamber, and a second opening. The drape and bag are constructed such that when they are in their normal operational position, they are positioned such that the surgical site is above and in fluid communication with the first opening, the first opening is above and in fluid communication with the lower chamber, and the second opening is above and in fluid communication with the lower chamber.

9 Claims, 8 Drawing Figures

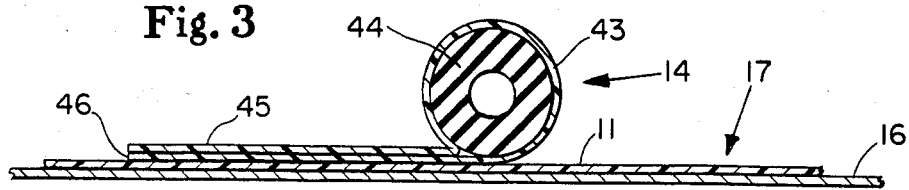
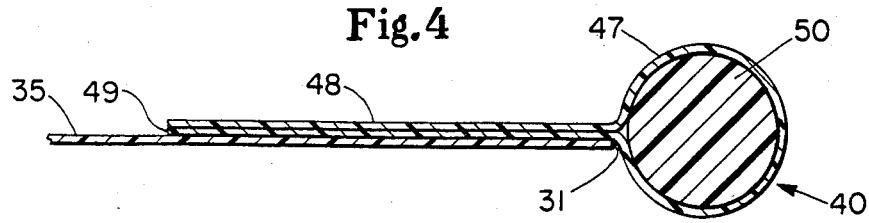
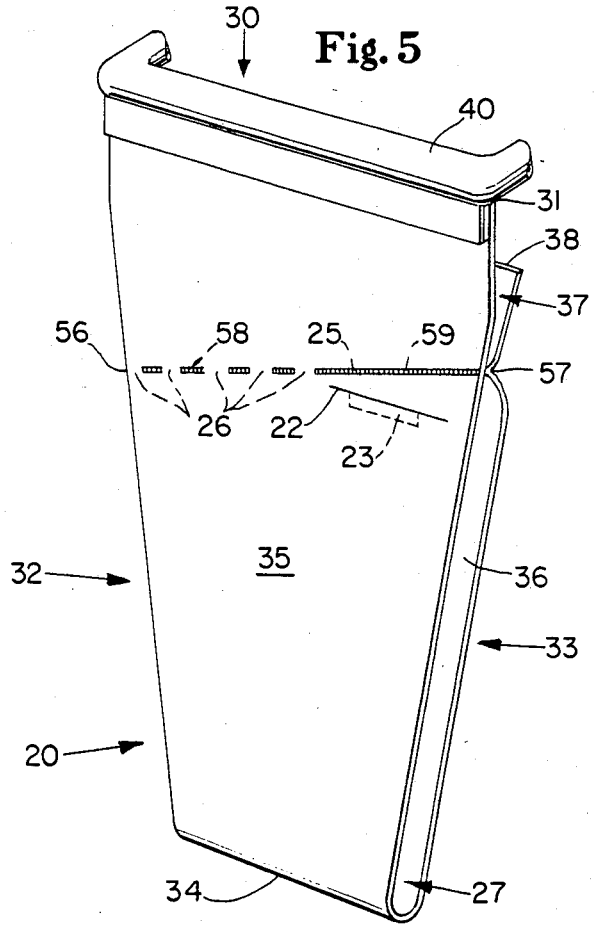

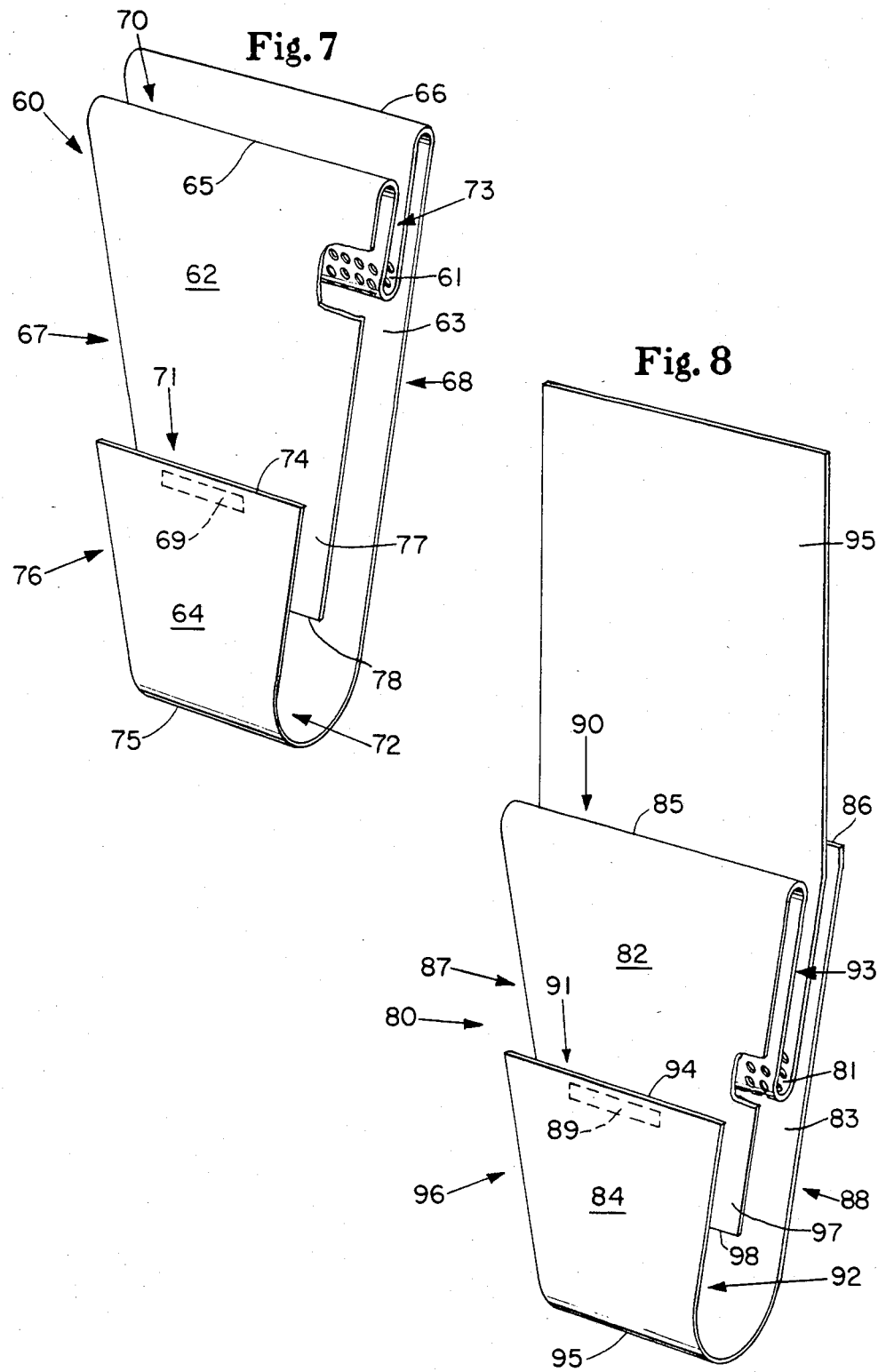

SURGICAL DRAPE WITH FLUID COLLECTION BAG

TECHNICAL FIELD

This invention relates to surgical drapes, especially to surgical drapes used for craniotomy surgical procedures; in particular, this invention relates to surgical drapes having a fluid collection bag attached thereto.

BACKGROUND OF THE INVENTION

A patient undergoing a surgical procedure is generally at least partially covered by a surgical drape. The surgical procedure is often performed through a fenestration or opening in the drape. The drape performs serveral functions during the operation. Surgical drapes are sterilized prior to use so that the drape provides a protective barrier between the nonsterile patient and operating table and the sterile clothing of the surgeon. Single use, disposable surgical drapes are commonly used; such drapes generally are sterile and prefolded in a protective package, ready for draping over the patient.

Another function of surgical drapes is to disperse fluid runoff from the surgical site so that it does not obstruct the working of the surgeon and so that it does not soil the patient. If there is only a small amount of fluid runoff from the surgical site, it may be simply dispersed across the surface of the drape; some drapes are produced with an absorbent upper surface in order to absorb such fluid runoff. Where a substantial amount of fluid runoff is expected from the surgical site, means for channeling that fluid into an appropriate receptacle may be provided by the drape. Such drapes are disclosed in U.S. Pat. Nos. 759,084 issued to Eggers and Stahl on May 3, 1904, and 3,650,267 issued to Anderson on Mar. 21, 1972.

Drapes may have pouches built into or attached to the drapes in order to capture fluid runoff from the surgical site. Drapes with such pouches are disclosed in U.S. Pat. Nos. 3,791,382 issued to Collins on Feb. 12, 1974, and 4,323,062 issued to Canty on Apr. 6, 1982.

Pouches or bags or similar apparatus have been used to collect fluid runoff from a surgical site in order to measure the quantity of fluid draining from the site. Such pouches or bags are disclosed in U.S. Pat. Nos. 3,199,507 issued to Kamm on Aug. 10, 1965; 3,364,928 issued to Creager, Zinck and Pereny on Jan. 23, 1968; 3,386,444 issued to Brenner and Reser on June 4, 1968; 3,575,225 issued to Muheim on Apr. 20, 1971; and 4,007,741 issued to Waldrop and Brantley on Feb. 15, 1977.

Drapes designed primarily for use in craniotomy surgical procedures are disclosed in U.S. Pat. Nos. 3,911,912 issued to Krebs and Arps on Oct. 14, 1975; 3,952,738 issued to Krzewinski on Apr. 27, 1976; and 3,955,569 issued to Krzewinski and Gorrie on May 11, 1976.

A large amount of fluid runoff from the surgical site is often associated with craniotomy surgery. Fluid collection bags may be attached to craniotomy drapes in order to capture such fluid runoff. Fluid collection bags for craniotomy drapes are disclosed in U.S. Pat. No. 4,169,472 issued to Morris on Oct. 2, 1979, and in a sales brochure entitled "Steri-Drape Irrigation Pouch" issued by the Surgical Products Division of the 3M Company, St. Paul, Minn. (undated).

SUMMARY OF THE INVENTION

It is an object of the present invention to provide a surgical drape with an attached bag for collection of fluid runoff from the surgical site.

It is a further object of the present invention to provide such a bag for collection of fluid for measurement or sampling as desired.

It is a still further object of the present invention to provide such a bag having a means for convenient removal of fluid from the bag.

It is a further object of the present invention to provide such a bag having a means for separating solid objects from fluid flowing into the bag.

It is also an object of the present invention to provide such a drape having an improved means for channeling fluid from the surgical site into the bag.

It is a further object of the present invention to provide such a bag having an improved means for holding the bag open to allow fluid to enter the bag.

A surgical drape comprises an upper surface and a surgical site, and has a fluid collection bag attached to the upper surface of the drape. The bag comprises a first opening, a lower, fluid-collection chamber, and a second opening. The drape and bag are constructed such that when the drape and bag are in their normal operational position, they are positioned such that the surgical site is above and in fluid communication with the first opening, the first opening is above and in fluid communication with the lower chamber, and the second opening is above and in fluid communication with the lower chamber. Fluid runoff from the surgical site flows by gravity means to and through the first opening of the bag and into the lower chamber of the bag.

BRIEF DESCRIPTION OF THE DRAWINGS

FIG. 3 is a cross-sectional view taken along section line 3—3 of the drape of FIG. 2.

FIG. 4 is a cross-sectional view taken along section line 4—4 of the bag of FIG. 2.

FIG. 5 is a fragmentary perspective view of the fluid collection bag of FIG. 3 with the sides of the bag unsealed (to show construction of the bag).

FIG. 7 is a fragmentary perspective view of an alternate fluid collection bag with the sides of the bag unsealed (to show construction of the bag).

FIG. 8 is a fragmentary perspective view of another alternate fluid collection bag with the sides of the bag unsealed (to show construction of the bag).

DETAILED DESCRIPTION OF THE INVENTION

Figure 1:
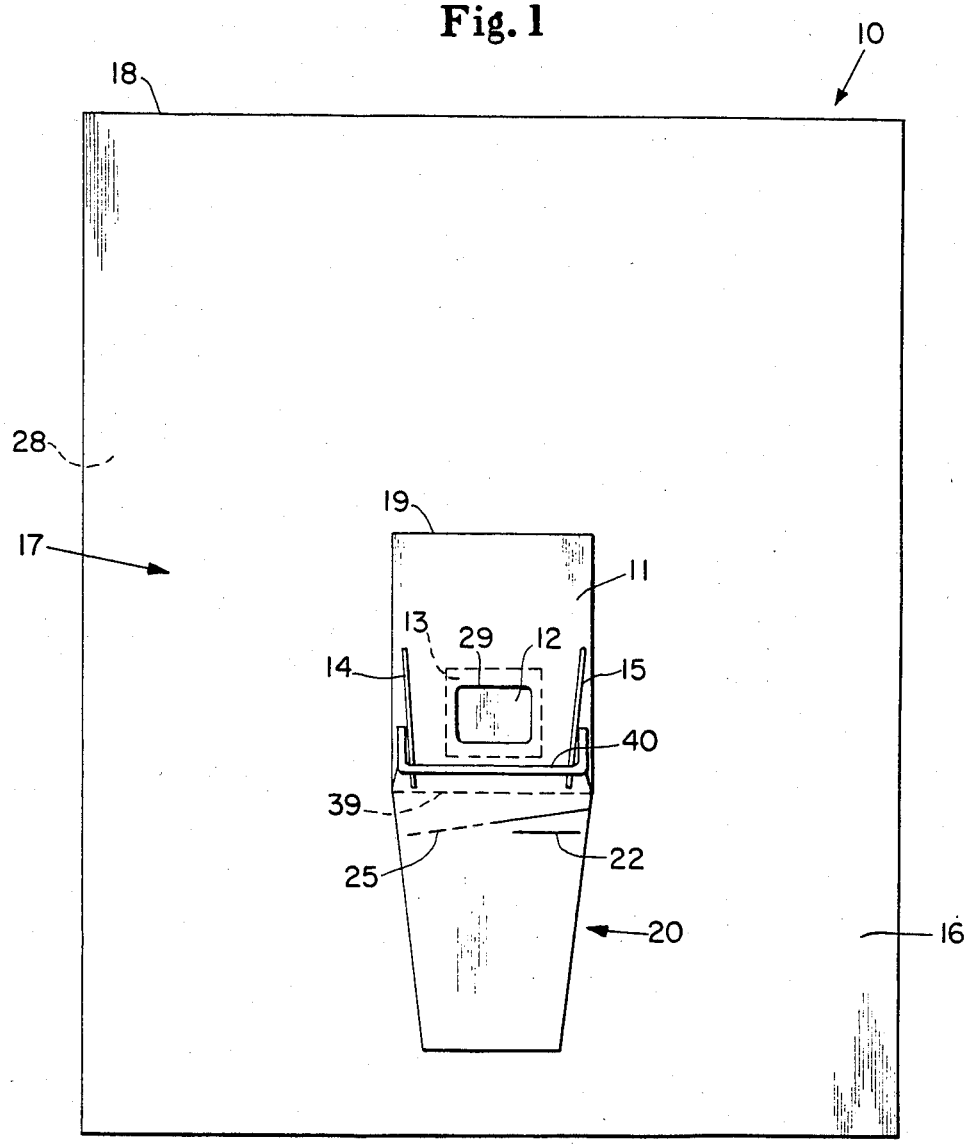
FIG. 1 is a plan view of a craniotomy drape with a fluid collection bag attached.

Referring to the drawings wherein like referenced characters are utilized to identify like parts throughout the several views, there is illustrated in FIG. 1 surgical drape 10 which is particularly adapted for use in craniotomy surgical procedures. In a preferred embodiment, drape 10 comprises base sheet 16 which is a nonwoven fabric laminate such as that described in U.S. Pat. No. 4,113,911 issued to LaFitte and Camden on Sept. 12, 1978, the disclosure of which is hereby incorporated by reference. Drape 10 preferably has reinforcement patch 11 in the central portion of drape 10. Reinforcement patch 11 is preferably a fluid-impervious material adhered to the upper surface of base sheet 16. A preferred reinforcement patch material is a plastic film about 0.09 mm in thickness.

Drape 10 is typically rectangular with dimensions of 281 cm wide by 274 cm long. Reinforcement patch 11 is typically also rectangular with dimensions of 51 cm wide by 96 cm long. Reinforcement patch 11 is preferably centrally located across the width of drape 10, and edge 19 of reinforcement patch 11 is typically 112 cm from edge 18 of drape 10.

There is preferably located within reinforcement patch 11 fenestration 12 at the surgical site for drape 10 through which a surgical procedure is performed. Fenestration 12 is typically 15 cm by 15 cm with 5 cm radius corners. Fenestration 12 is typically centrally located across the width of reinforcement patch 11 and edge 29 of fenestration 12 is typically 38 cm from edge 19 of reinforcement patch 11.

Pressure sensitive adhesive 13, typically about 5 cm wide, preferably surrounds fenestration 12 on undersurface 28 of base sheet 16. Adhesive 13 is used to adhere drape 10 securely to the patient around fenestration 12; this prevents fluid runoff from the surgical site from soiling the patient beyond the portion of the patient exposed through fenestration 12. Prior to use of drape 10, adhesive 13 is covered by a release paper which is peeled off in order to adhere drape 10 to the patient.

Figure 2:
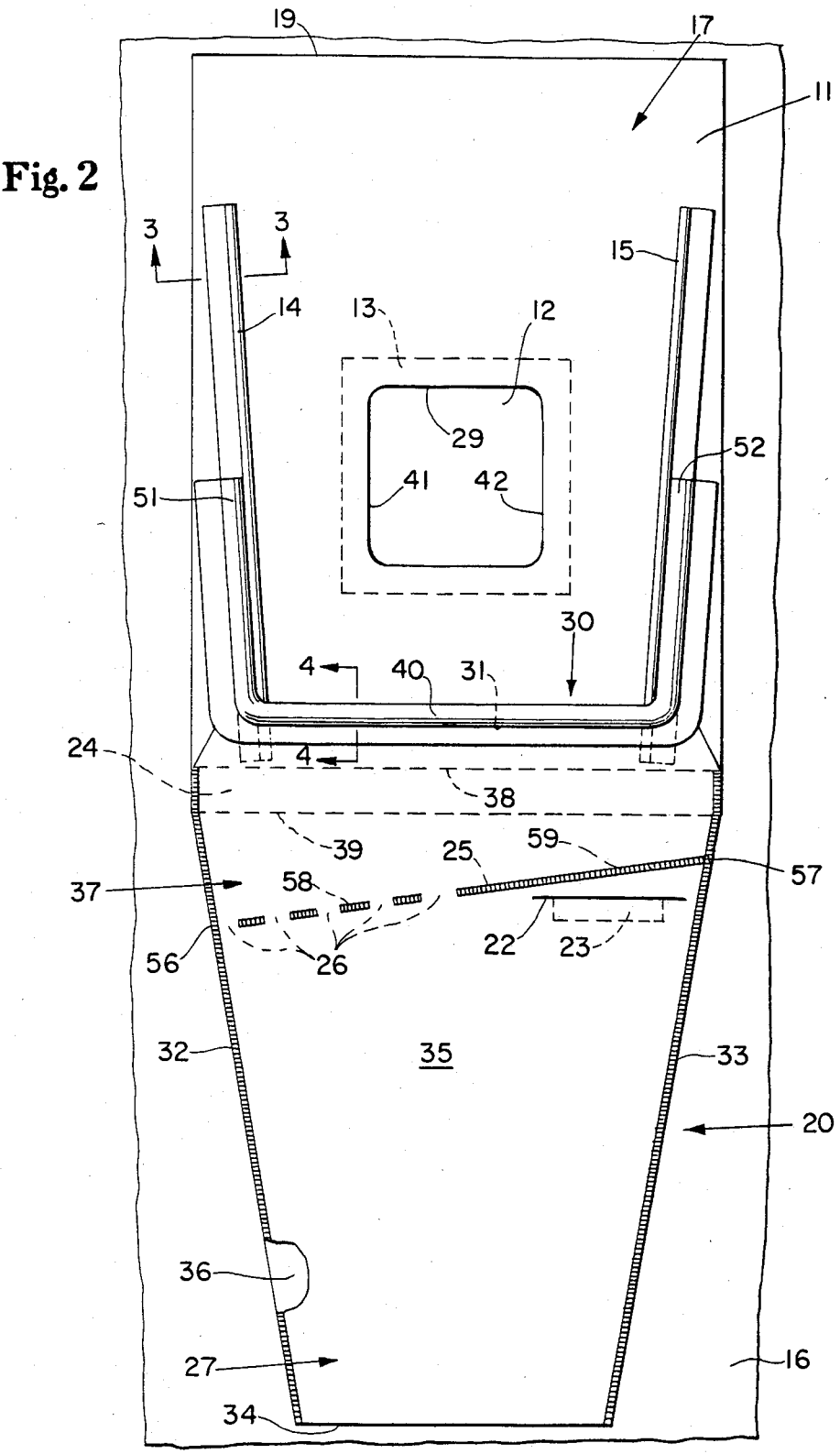
FIG. 2 is an enlarged fragmentary plan view of the fenestration area and attached fluid collection bag of the drape of FIG. 1.

Fluid collection bag 20, which is shown in greater detail in FIG. 2, is preferably constructed of a flexible, fluid-impervious sheet material, more preferably of an inexpensive material such as a plastic film. It is preferred that bag 20 be made of a substantially clear material to allow inspection of collected fluid through the bag material. A most preferred material used for making bag 20 is a proprietary polyethylene copolymer film, Elastoflex E-548 supplied by Clopay Corporation, Cincinnati, Ohio, of about 0.09 mm thickness. Elastoflex E-548 is a quiet, drapable, clear plastic film.

Fluid collection bag 20 is preferably attached to upper surface 17 of drape 10 along edge 39 of reinforcement patch 11. Bag 20 has a first opening 30 which is in fluid communication with the surgical site at fenestration 12 when drape 10 and bag 20 are in their normal operational position on a patient.

Fluid collection bag 20 is preferably constructed such that front panel 35 has top edge 31 and back panel 36 has top edge 38. With this construction, first opening 30 is a top opening between top edge 31 of front panel 35 and top edge 38 of back panel 36. Bag 20 is closed along left side 32, right side 33, and bottom edge 34, thus forming lower, fluid-collection chamber 27 having enclosed sides and bottom and an open top. Sides 32 and 33 and bottom edge 34 of bag 20 are preferably closed by having front panel 35 and back panel 36 sealed to one another along sides 32 and 33 and bottom edge 34. Such sealing can be achieved, for example, by adhering front panel 35 and back panel 36 by heat sealing, by use of adhesives, or by panels 35 and 36 being contiguous panels of a single piece of material.

Fluid collection bag 20 is preferably constructed of a single piece of plastic film, as illustrated in FIG. 5 (without sides 32 and 33 sealed in order to show the construction of the bag). The film piece can typically be 152 cm long and 51 cm wide. The film piece is folded across its width, the fold becoming bottom edge 34 of bag 20, and the ends of the film piece forming top edge 31 of front panel 35 and top edge 38 of back panel 36 of bag 20, Front panel 35 is typically 81 cm long and back panel 36 is typically 71 cm long. Sides 32 and 33 are preferably heat sealed thus adhering front panel 35 to back panel 36 along tapered lines from top edge 38 of back panel 36 to bottom edge 34. Bottom edge 34 of bag 20 is typically about 30 cm wide.

Fluid collection bag 20 is adhered to drape 10 by any conventional adhering means, preferably in a manner such that top edge 38 of back panel 36 is parallel to and overlaps edge 39 of reinforcement patch 11. A suitable means for adhering bag 22 to drape 10 is by use of adhesive strip 24 which is preferably adjacent top edge 38 of back panel 36 and is typically 5 cm wide.

When drape 10 and bag 20 are in their normal operational position on a patient, the surgical site at fenestration 12 is in fluid communication with first opening 30 of bag 20 in that fluid can flow from the surgical site at fenestration 12 across reinforcement patch 11 to first opening 30 of fluid collection bag 20. First opening 30 is in fluid communication with lower chamber 27 in that fluid entering first opening 30 of bag 20 can flow into lower chamber 27. Fluid collection bag 20 preferably has an upper chamber 37 above lower chamber 27 with a screening means between them. Lower chamber 27 is in fluid communication with upper chamber 37 through the screening means, and upper chamber 37 is in fluid communication with top opening 30.

The screening means between upper chamber 37 and lower chamber 27 of fluid collection bag 20 shown in FIG. 2 is a line of adherence 25 between front panel 35 and back panel 36. Line 25 extends from point 56 at left side 32 to point 57 at right side 33 of bag 20. Line 25 is preferably slanted. For example, as shown in FIG. 2, line 25 slants from higher point 57 typically 20 cm from top edge 31 of front panel 35 at right side 33 to lower point 56 typically 28 cm from top edge 31 of front panel 35 at left side 32, such that line 25 has lower segment 58 toward side 32 and higher segment 59 toward side 33 of bag 20.

Line 25 has nonadhered gaps 26 therein which provide the fluid communication between upper chamber 37 and lower chamber 27 of bag 20. When line 25 is slanted, gaps 26 are preferably located in lower segment 58 of line 25. A typical gap arrangement, as shown in FIG. 2, is to have five gaps 26, each about 2.5 cm wide, with about 2.5 cm in between each gap 26, with one gap being located at the lowest point of line 25 proximate side 32 of bag 20.

Line 25 with gaps 26 acts as a screening means between upper chamber 37 and lower chamber 27 of bag 20 to hold large solid objects near the top of bag 20 for later recovery and inspection if desired. Examples of solid objects which are likely to flow into bag 20 through top opening 30 include surgical sponges and large bone chips. Fluid flowing into bag 20 readily flows through gaps 26 into lower chamber 27 so that such solid objects are readily located atop the screening means.

Bag 20 has second opening 22 which is above and in fluid communication with lower chamber 27 when drape 10 and bag 20 are in their normal operational position on a patient. Second opening 22 provides an access to fluid which collects in lower chamber 27. Second opening 22 is preferably located in front panel 35 of bag 20 beneath a segment of line 25 which has no gaps. Second opening 22 is preferably a slit in front panel 35 located toward side 33 of bag 20 beneath higher segment 59 of line 25. If fluid collects in lower chamber 27 and becomes heavy such that it puts a strain on drape 10, the fluid can be discharged through opening 22 by means of suction tubing or other convenient means. There is preferably a pressure sensitive adhesive strip 23 located on the inner surface of front panel 35 along the lower edge of opening 22 for adhering such suction tubing in place.

Higher segment 59 of line 25 which has no gaps is a passive (no moving parts) blocking means between top opening 30 and slit opening 22. When drape 10 and bag 20 are in their normal operational position on a patient, such blocking means prevents gravity flow of fluid from top opening 30 directly to slit opening 22; thus any fluid flowing into bag 20 collects in lower chamber 27 until it is desired to discharge the fluid through slit opening 22.

In order to assist fluid runoff from the surgical site to flow into fluid collection bag 20, fluid control rails 14 and 15 are preferably located alongside but spaced from fenestration 12 and extending to top opening 30 of bag 20. Rails 14 and 15 are attached along their entire length to upper surface 17 of drape 10. When bag 20 and drape 10 are in their normal operational position, fluid runoff from the surgical site may flow to and strikes the rails. The fluid is blocked from flowing past the rails and is deflected and channeled into fluid collection bag 20. Rails 14 and 15 are typically about 51 cm long and preferably extend from top opening 30 near sides 32 and 33 of bag 20 parallel to or at a slight angle to sides 41 and 42 of fenestration 12.

Rails 14 and 15 must be very flexible to allow drape 10 to assume a variety of contours. Yet rails 14 and 15 must be constructed such that they remain raised above upper surface 17 of drape 10 even when drape 10 undergoes sharp contour changes.

FIG. 3 is a cross-sectional view of rail 14 taken along section line 3—3 of FIG. 2. It shows a preferred construction of rail 14 which is made from a length of flexible tubing 44 encased in a flexible sheet material 43, preferably a fluid-impervious plastic film such as an Elastoflex E-548 film. Edges 45 and 46 of film 43 are adhered together, preferably with adhesive, to contain tubing 44 within film 43. Edge 46 of film 43 is then adhered to upper surface 17 of drape 10, preferably by adhesive or by heat sealing. Tubing 44 is preferably thick-walled so that it does not collapse when it undergoes sharp contour changes. Tubing 44 is preferably a rubber surgical tubing typically about 10 mm in diameter with a wall thickness of about 2½ mm.

It is desirable that top edge 31 of front panel 35 of bag 20 be kept apart from upper surface 17 of drape 10 when drape 10 and bag 20 are in their normal operational position, so that top opening 30 remains open during the surgical procedure to receive fluid flowing toward it. It is therefore preferred that a means for keeping top opening 30 open be employed.

A preferred opening means 40 is shown in FIGS. 2 and 4 where FIG. 4 is a cross-sectional view taken along section line 4—4 of FIG. 2. Opening means 40 is made from rod 50 of a flexible material which is preferably encased in a flexible sheet material 47, preferably a fluid-impervious plastic film such as an Elastoflex E-548 film. Edges 48 and 49 of film 47 are adhered together to encase rod 50. Edge 49 of film 47 is adhered, preferably by adhesive or heat sealing, preferably along the entire length of top edge 31 of front panel 35 of bag 20. Ends 51 and 52 of opening means 40 which preferably extend beyond sides 32 and 33 of bag 20 are preferably bent and adhered to upper surface 17 of drape 10, preferably by adhesive or heat sealing.

Rod 50 is preferably a material which is flexible, yet has sufficient stiffness to hold top opening 30 of bag 20 open. A preferred material for rod 50 is a flexible polymeric foam rod, especially preferred is a polyethylene foam rod. A typical diameter of such rod is about 17 mm. Such foam rod can be obtained from Styro-Floral Products, Inc. of Memphis, Tenn., under the tradename HBR.

Figure 6:
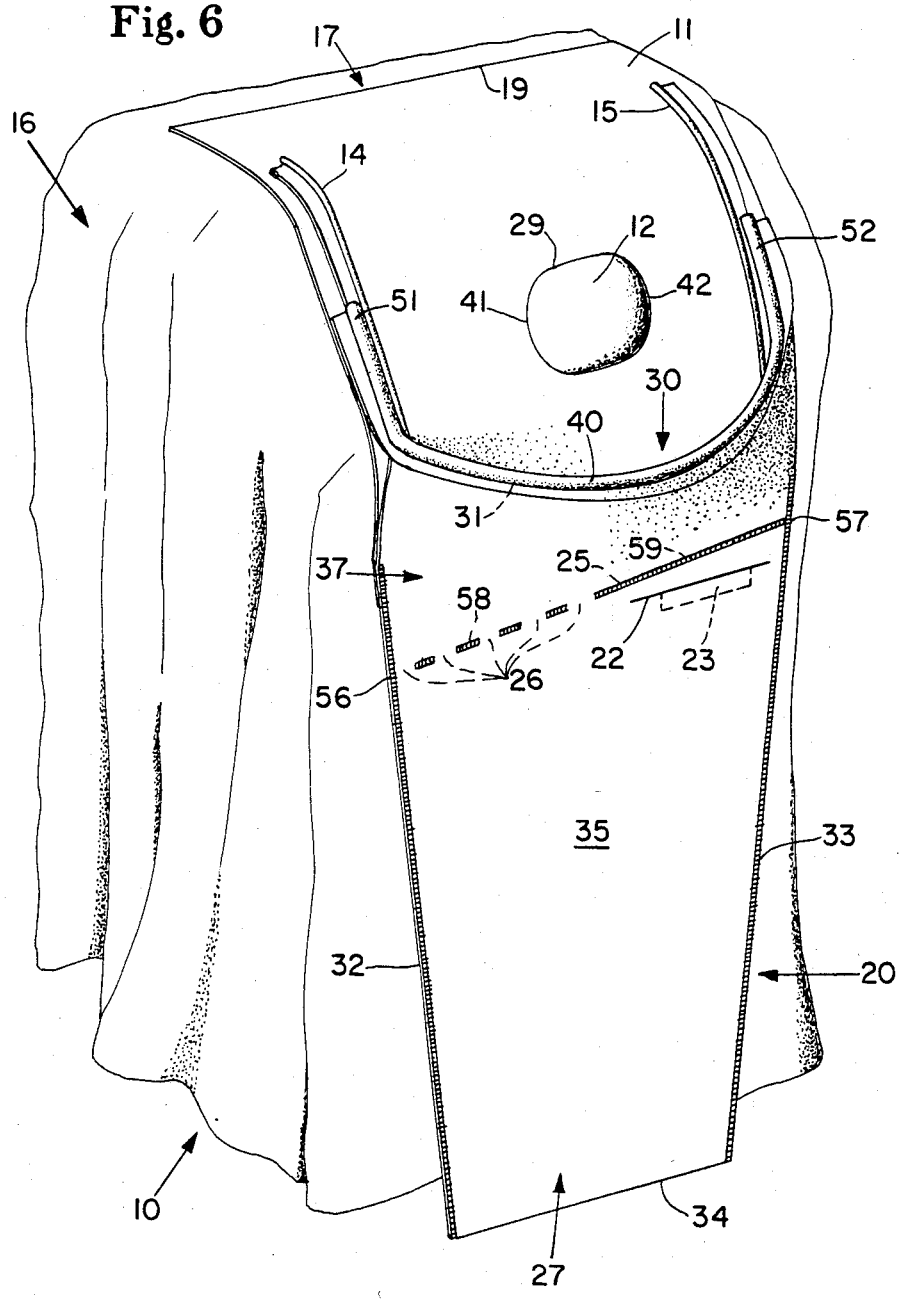
FIG. 6 is a fragmentary perspective view of the craniotomy drape of FIG. 1 applied to a patient in position for use.

FIG. 6 is a perspective layout of drape 10 of FIG. 1 as seen placed over a patient and ready for a craniotomy surgical procedure. When placed in such a normal operational position, drape 10 and bag 20 are positioned such that the surgical site at fenestration 12 is above top opening 30, top opening 30 is above upper chamber 37 which is above lower chamber 27, and slit opening 22 is above lower chamber 27. A major portion of fluid runoff from the surgical site at fenestration 12 flows by gravity means, possibly being deflected by rails 14 and 15, to bag 20 and through top opening 30 into upper chamber 37 of bag 20. Such fluid further flows by gravity means from upper chamber 37 through the screening means, e.g. gaps 26 of line of adherence 25, into lower chamber 27 of bag 20. The fluid cannot flow by gravity means from lower chamber 27. Because of this, the fluid collected in lower chamber 27 can be measured or sampled prior to discarding if desired.

Fluid which has collected in lower chamber 27 of bag 20 can conveniently be discharged through slit opening 22 if desired. The usual manner of discharging such fluid from lower chamber 27 is by insertion of a suction tube into lower chamber 27 through opening 22 and suctioning the fluid from lower chamber 27.

A passive blocking means, e.g. higher segment 59 of line of adherence 25 which is without gaps and is located above slit opening 22, prevents fluid from flowing directly from top opening 30 to opening 22 by gravity means. Such blocking means causes the fluid to be collected in lower chamber 27 of bag 20.

FIG. 7 is a perspective view of an alternate fluid collection bag 60 which is also preferably constructed of a single piece of clear, flexible, fluid-impervious sheet material such as plastic film. Bag 60 is shown with sides 67 and 68 of the bag unsealed in order to show how bag 60 is constructed from a single piece of film.

Bag 60 has front panel 76 comprised of two overlapping sections, top front section 62 with top edge 65 and bottom edge 78, and bottom front section 64 with top edge 74. Bag 60 has back panel 63 with top edge 66. First opening 70 of bag 60 is a top opening between top edge 65 of top front section 62 of front panel 76 and top edge 66 of back panel 63.

Bag 60 is preferably attached to a drape such that top edge 66 of back panel 63 is parallel to and overlaps one edge of a reinforcement patch of a drape, e.g. edge 39 of patch 11 of drape 10 of FIG. 1. Thus when bag 60 is in its normal operational position on a drape placed over a patient, top opening 70 is in fluid communication with the surgical site. Fluid runoff from the surgical site flows by gravity means to and enters into bag 60 through top opening 70. Top opening 70 is in fluid communication with lower chamber 72 of bag 60 such that fluid flows by gravity means through top opening 70 and thence into lower chamber 72 of bag 60.

In a preferred embodiment, screening means 61 separates upper chamber 73 from lower chamber 72 of bag 60. Screening means 61 is preferably a portion of the material from which bag 60 is made in which holes have been perforated in order to allow fluid to flow through screening means 61. Large solid objects, such as surgical sponges and bone chips, are retained in upper chamber 73 by screening means 61.

When bag 60 is in its normal operational position, upper chamber 73 is in fluid communication with top opening 70, and with lower chamber 72 of bag 60 through the holes in screening means 61. Fluid flows by gravity means from upper chamber 73 through screening means 61 into lower chamber 72 where it collects.

Top edge 74 of bottom front section 64 overlaps top front section 62 of front panel 76 of bag 60 to provide second opening 71 between bottom section 64 and top section 62. Opening 71 provides a means for discharging fluid from lower chamber 72 of bag 60. In particular, opening 71 provides access for suction tubing to withdraw fluid from lower chamber 72 in the same manner as described for bag 20 through opening 22 hereinbefore. Adhesive strip 69 provides a means for anchoring such suction tubing in lower chamber 72 of bag 60.

Bottom section 64 overlaps top section 62 of front panel 76 such that when bag 60 is in its normal operational position, top edge 74 of bottom section 64 is above lower edge 78 of top section 62. This construction results in lower portion 77 of top section 62 functioning as a passive blocking means to prevent fluid from flowing by gravity means directly from top opening 70 to opening 71. Thus fluid is collected in lower chamber 72 of bag 60 until it is desired to discharge the fluid through opening 71 by means of suction tubing or other means.

Fluid collection bag 60 is preferably constructed from a single piece of plastic film, typically about 51 cm wide by 205 cm long. A portion of the film is perforated to provide for screening means 61. Folds are made across the film to form top edge 65 of top front section 62, the bottom of screening means 61, top edge 66 of back panel 63, and bottom edge 75 of bag 60. The ends of the piece of film are overlapped; these ends correspond to top edge 74 of bottom front section 64 and bottom edge 78 of top front section 62 of front panel 76.

Sides 67 and 68 of bag 60 are sealed, preferably either by heat sealing or adhesive. Sides 67 and 68 are preferably sealed such that bag 60 tapers such that bottom end 75 is narrower than top opening 70 of bag 60, similar to bag 20 as described hereinbefore. Excess film is trimmed from sides 67 and 68 when the bag is tapered in this manner.

FIG. 8 is a perspective view of another alternate fluid collection bag 80. Bag 80 is preferably constructed of two pieces of clear, flexible, fluid-impervious sheet material such as plastic film. Bag 80 is shown in FIG. 9 with sides 87 and 88 of the bag unsealed in order to show how bag 80 is constructed.

Bag 80 has front panel 96 comprised of two overlapping sections, top front section 82 with top edge 85 and bottom edge 98, and bottom front section 84 with top edge 94. Bag 80 has back panel 83 with top edge 86.

One piece of film is preferably used to make back panel 83 and bottom front section 84 of front panel 96 with a single fold at bottom edge 95 of bag 80. The second piece of film preferably forms top front section 82 of front panel 96 and screening means 81 by perforating the appropriate portion of the piece of film. Extension 95 from screening means 81 extends substantially beyond top edge 86 of back panel 83 and is used to form the reinforcement patch for the drape to which bag 80 is adhered.

Bag 80 is formed by sealing sides 87 and 88, preferably by heat sealing or adhesive, as described hereinbefore for bags 20 and 60. Resulting bag 80 is preferably structurally the same as bag 60 except that the reinforcement patch is integrally connected to the bag instead of the bag being adhered to a drape with the top edge of the back panel parallel to and overlapping an edge of the patch.

The functional use of bag 80 is preferably identical to that of bag 60 described hereinbefore. Bag 80 thus has top opening 90 between top edge 85 of top front section 82 of front panel 96 and extension 95. When bag 80 is in its normal operational position, top opening 90 is in fluid communication with upper chamber 93 of bag 80. Upper chamber 93 is in fluid communication with lower chamber 92 through the perforations in screening means 81. Top edge 94 of bottom front section 84 overlaps bottom edge 98 of top front section 82 of front panel 96, thus forming second opening 91 through which suction tubing can be inserted in order to withdraw fluid from lower chamber 92 of bag 80. Adhesive strip 89 provides a means for anchoring such tubing. Bottom portion 97 of top front section 82 functions as a passive blocking means to prevent fluid from flowing by gravity means directly from top opening 90 to opening 91. Extension 95 is adhered to a base drape material to provide a reinforcement patch and a fenestration is then preferably cut through extension 95 and the base drape material at the surgical site for the drape.

While particular embodiments of the present invention have been illustrated and described, those skilled in the art will recognize that various changes and modifications can be made without departing from the spirit and scope of the invention. It is intended to cover, in the appended claims, all such modifications that are within the scope of this invention.

What is claimed is:

1. A surgical drape comprising:
   (a) A base sheet constructed of a nonwoven fabric laminate having an upper surface and a lower surface;
   (b) A surgical site centrally located across the width of said upper surface of said base sheet through which a surgical procedure is performed;
   (c) A fluid collection bag constructed of a flexible, fluid impervious sheet material comprising a front panel having a top edge, a left side, a right side, and a bottom edge; a back panel having a top edge, a left side, a right side, and a bottom edge; said left and right sides, and said bottom edges being closed; said top edge of said back panel being secured to said upper surface of said base sheet; a first opening formed by the open top edges of said front and back panels, said first opening being in fluid communication with said surgical site; a lower chamber located below and in fluid communication with said first opening; and a second opening in said front panel located above said lower chamber so as to prevent fluid discharge by gravity through said second opening and to enable the insertion of fluid discharge means and the measurement and sampling of fluid,
   (d) Fluid control rails attached to said upper surface of said base sheet, said rails being located alongside but spaced from said surgical site such that when said base sheet and said bag are in their normal operational position, fluid runoff from said surgical site which flows to and strikes said rails is channeled to said first opening of said bag, said rails being constructed of a flexible, thick-walled tubing encased in a flexible sheet material; and (e) Means for holding said first opening in an open position when said base sheet and said bag are in their normal operational position, said opening means comprising a flexible, polymeric foam rod encased in a flexible sheet material, a middle section of said encased rod being attached to said top edge of said front panel of said bag, and the ends of said rod being attached to said upper surface of said base sheet.

2. The drape of claim 1 wherein said surgical site comprises a reinforcement patch of fluid-impervious material that is adhered to said upper surface of said base sheet, and a fenestration located within said reinforcement patch.

3. The drape of claim 2 wherein said fluid control rails are attached to said upper surface of said drape, said rails being located alongside but spaced from said fenestration.

4. The drape of claim 1 wherein said flexible, thick-walled tubing of said fluid control rails is rubber surgical tubing, and wherein said flexible, polymeric foam rod is a polyethylene foam rod.

5. The drape of claim 1 wherein said fluid collection bag further comprises passive blocking means between said first opening and said second opening to prevent fluid to flow by gravity from said first opening directly to said second opening so that all of the fluid is first collected in said lower chamber.

6. The drape of claim 5 wherein said fluid collection bag further comprises an upper chamber located above said lower chamber and in fluid communication with said lower chamber and said first opening; and integral screening means located between said upper chamber and said lower chamber.

7. The drape of claim 6 wherein said screening means is a portion of said bag material having perforations therein.

8. The drape of claim 7 wherein said fluid collection bag is constructed of a single piece of flexible, fluid impervious material, said bag further comprising said front panel having a top front section having a top edge and a bottom edge, and a bottom front section having a top edge; wherein said top edge of said bottom front section overlaps said top front section to form said second opening; and wherein said bottom edge and the bottom portion of said top front section form said passive blocking means.

9. The drape of claim 7 wherein said fluid collection bag is constructed of a first piece of material and a second piece of material; said front panel of said fluid collection bag having a top front section having a top edge and a bottom edge, and a bottom front section having a top edge; wherein said first piece of material is folded to form said back panel and said bottom front section of said front panel; wherein said second piece of material is folded to form said screening means and said top front section of said front panel; wherein said top edge of said bottom front section overlap said bottom edge of said top front section to form said second opening; and wherein said bottom edge and the bottom portion of said top front section form said passive blocking means.

* * * * *